United States Patent [19]
Newman

[11] Patent Number: 5,887,477
[45] Date of Patent: Mar. 30, 1999

[54] APPARATUS AND METHOD FOR TESTING WATERPROOFNESS AND BREATHING FABRICS

[75] Inventor: James R. Newman, Hillsboro, Oreg.

[73] Assignee: Nike, Inc., Beaverton, Oreg.

[21] Appl. No.: 842,681

[22] Filed: Apr. 15, 1997

[51] Int. Cl.⁶ .................................................. G01N 15/08
[52] U.S. Cl. .............................................. 73/159; 73/38
[58] Field of Search .................................... 73/38, 159

[56] References Cited

U.S. PATENT DOCUMENTS

| | | | |
|---|---|---|---|
| 1,538,793 | 5/1925 | Gallagher et al. | 73/38 |
| 1,660,024 | 2/1928 | Abrams | 73/38 |
| 1,827,562 | 10/1931 | Carpenter | 73/38 |
| 2,054,204 | 9/1936 | McDonald . | |
| 2,118,906 | 5/1938 | Troxel . | |
| 3,166,439 | 1/1965 | Dennhofer . | |
| 3,548,634 | 12/1970 | Roy | 73/38 |
| 4,581,921 | 4/1986 | Gillespie et al. . | |
| 4,776,209 | 10/1988 | Patchel . | |
| 4,799,384 | 1/1989 | Casali . | |
| 4,846,970 | 7/1989 | Bertelsen et al. . | |
| 4,918,981 | 4/1990 | Gore . | |
| 5,390,531 | 2/1995 | Taylor . | |

*Primary Examiner*—Richard Chilcot
*Assistant Examiner*—Willie Morris Worth
*Attorney, Agent, or Firm*—Banner & Witcoff, Ltd.

[57] ABSTRACT

The apparatus for testing the characteristics of waterproofness and breathability of fabrics includes a demonstration unit, a base unit, and a fluid conduit and valve. The demonstration unit has a transparent wall and a support plate/gasket combination to retain and support the test fabric specimen. The flexible fluid conduit runs between the demonstration unit and the base unit, and a valve is positioned in the conduit. To test a fabric's waterproofness: the demonstration unit is assembled; the base unit is filled with water; the demonstration unit is placed lower than the base unit, and thus, water flows into the demonstration unit; and the demonstration unit is positioned to expose and view the fabric. To show the fabric's breathability: the demonstration unit, filled with water, is positioned higher than the base unit; the valve is opened causing the water to flow out of the demonstration unit; and air is drawn through a breathable fabric and is visible as bubbles rising from the fabric into the water contained in the demonstration unit.

12 Claims, 3 Drawing Sheets

APPARATUS AND METHOD FOR TESTING WATERPROOFNESS AND BREATHING FABRICS

FIELD OF THE INVENTION

The present invention relates to the testing and demonstration of the waterproofness and the breathability of fabrics. More specifically, the present invention relates to a compact apparatus that can separately demonstrate the waterproofness of a fabric and the breathability of a fabric. Furthermore, the present invention is manually operated, and does not require an electrical power source.

BACKGROUND OF THE INVENTION

A variety of techniques have been developed to test both the waterproofness and breathability of fabrics and articles of clothing. Waterproofness is the capacity of a specimen to keep liquid water from penetrating. One way to test for waterproofness is to fill the test specimen with water and then check for the presence of leaks, or liquid water on the test specimen's outer surface. Breathability is the capacity of a specimen to allow gas to penetrate. When testing a specimen's breathability, the test specimen is typically inflated with gas at a pressure above atmospheric pressure. The test specimen's capacity to allow gas to penetrate is detected by loss of inflation pressure or air bubbles.

One common test of a specimen's waterproofness is to inflate the article and then immerse the inflated article in water. The absence of bubbles escaping from the inflated test specimen is used to demonstrate that the specimen is waterproof. Leaks occur when either a liquid or a gas penetrates a test specimen, whether through the fabric, at the seams, or through material defects. A water leak indicates that the specimen is not waterproof; a gas leak indicates that the specimen allows gas to penetrate. Thus, the presence of bubbles would indicate that the test specimen has a gas leak.

U.S. Pat. No. 4,799,384 to Casali discloses an apparatus and method for testing for gas leaks in order to demonstrate the waterproofness of footwear articles. In operation, the footwear article is inflated using compressed gas, the top of the article is gripped in such a manner that the gas cannot escape, the article is then immersed in a liquid reservoir which has at least one transparent side. The test article is observed for gas leaks as indicated by the presence of rising bubbles.

U.S. Pat. No. 3,166,439 to Dennhofer discloses an apparatus for examining surgical gloves for gas leaks. Dennhofer pressurizes the gloves with compressed gas while the gloves are under water and inspects for the presence of bubbles.

U.S. Pat. No. 2,054,204 to McDonald also discloses a device wherein surgical gloves can be tested for gas leaks. The sealed glove is placed in a mesh frame to prevent the glove from bulging when pressurized. A small hand pump is used to pressurize the sealed glove, and the pressurized glove within the mesh frame is immersed in a reservoir of water. Bubbles rising from the glove signal the presence of gas leaks.

U.S. Pat. No. 4,776,209 to Patchel discloses a gas leak detector for testing waterproofness wherein a glove or other article may be gas leak tested without getting the article wet. The article is positioned within a testing chamber and both the article and the test chamber are sealed. Gas at a controlled pressure is introduced into the sealed article. A tube fluidly connects the lower end of the test chamber with a reservoir of liquid. If gas leaks from the article into the test chamber, after the initial period of article inflation, then the gas inside the test chamber will exit through the tube into the liquid reservoir, and bubbles will visibly indicate this leakage.

Prior art references thus teach the presence of bubbles as indicative of a gas leak. However, such prior art references use gas pressure greater than ambient to generate bubbles. Furthermore, in such prior art devices a single test may be used to prove that a test specimen is both air tight and waterproof, i.e. if the test specimen does not leak air, it will not leak water.

Also known in the art are techniques for testing a specimen's moisture vapor transmissibility. For instance, U.S. Pat. No. 4,581,921 to Gillespie discloses a moisture vapor transmission test cell, having upper and lower enclosures with a test specimen positioned between the enclosures. Moisture vapor transmissibility is the capacity of a test specimen to allow air and water molecules to penetrate the specimen. Since water molecules are larger than air molecules, there is not an identical correspondence between breathability and moisture vapor transmissibility. A test specimen might let air penetrate, but not let the larger water molecules penetrate.

In Gillespie the upper enclosure contains flowing conditioned air; the lower enclosure contains a fluid/vapor reservoir. During operation, conditioned air flows parallel to the upper surface of a test specimen, while the lower surface of the test specimen is exposed to vapor of a test liquid contained in a reservoir. Vapor is drawn through the test specimen due to the flow of the conditioned air over the surface of the test specimen for a known period of time. At the end of a test cycle, the amount of fluid remaining in the reservoir is a measure of the moisture vapor transmissibility of the test specimen. Gillespie does not test or demonstrate the waterproofness of the test specimen, nor is there any visual display of the test specimen's breathability characteristics.

SUMMARY OF THE INVENTION

The apparatus for testing the characteristics of waterproofness and breathability of fabrics includes a demonstration unit, a base unit and, at least one flexible fluid conduit and a valve. The preferred embodiment of the demonstration unit includes a transparent wall and a support plate/gasket combination to retain and support the test fabric specimen and to form a demonstration reservoir. The base unit is also preferably made with a transparent wall, which together with a bottom wall forms a base reservoir. The flexible fluid conduit runs between the demonstration reservoir and the base reservoir, and the valve is positioned in the conduit. Further, a second fluid conduit with a pump in its flow path can be connected between the demonstration reservoir and the base reservoir. In a preferred embodiment, both the pump and the valve are manually operated.

The apparatus is used to demonstrate, preferably in a marketing/sales environment, the waterproofness and breathability of a swatch of test fabric. To test the fabric's waterproofness, the apparatus operates as follows: (1) the demonstration unit is assembled with a test fabric specimen extending over an opening in the demonstration reservoir; (2) the base reservoir is filled with water; (3) the demonstration unit is placed lower than the base unit, and thus, water flows by gravity into demonstration reservoir and completely fills the demonstration reservoir; and (4) the demonstration unit is positioned to expose and view the fabric. In a preferred technique, water is also pumped through the second fluid conduit into the demonstration reservoir to purge all air out of the demonstration reservoir and fluid conduits, and a valve in one of the conduits connecting the demonstration reservoir and the base reservoir is closed after the air is purged.

To show the fabric's breathability: (1) the demonstration unit is placed upright, i.e., with the fabric at the bottom of the demonstration reservoir, and positioned higher than the base unit; (2) the valve is opened causing the water to flow out of the demonstration reservoir and into the base reservoir; and (3) air, visible as tiny rising bubbles in the demonstration reservoir, is drawn through fabric which is breathable while the water flows out of the demonstration reservoir.

The present invention combines in a single apparatus the ability to conduct two distinct tests to separately demonstrate the breathability of a specimen and the waterproofness of the specimen. Further, the present invention draws air through the test specimen by creating a slight vacuum in the demonstration unit's reservoir. This vacuum is created by the action of the water in the demonstration reservoir flowing, under the force of gravity, down into the base reservoir. No, compressed air cylinders or pumps are needed to force air through the fabric.

DETAILED DESCRIPTION OF THE PREFERRED EMBODIMENT

Figure 1:
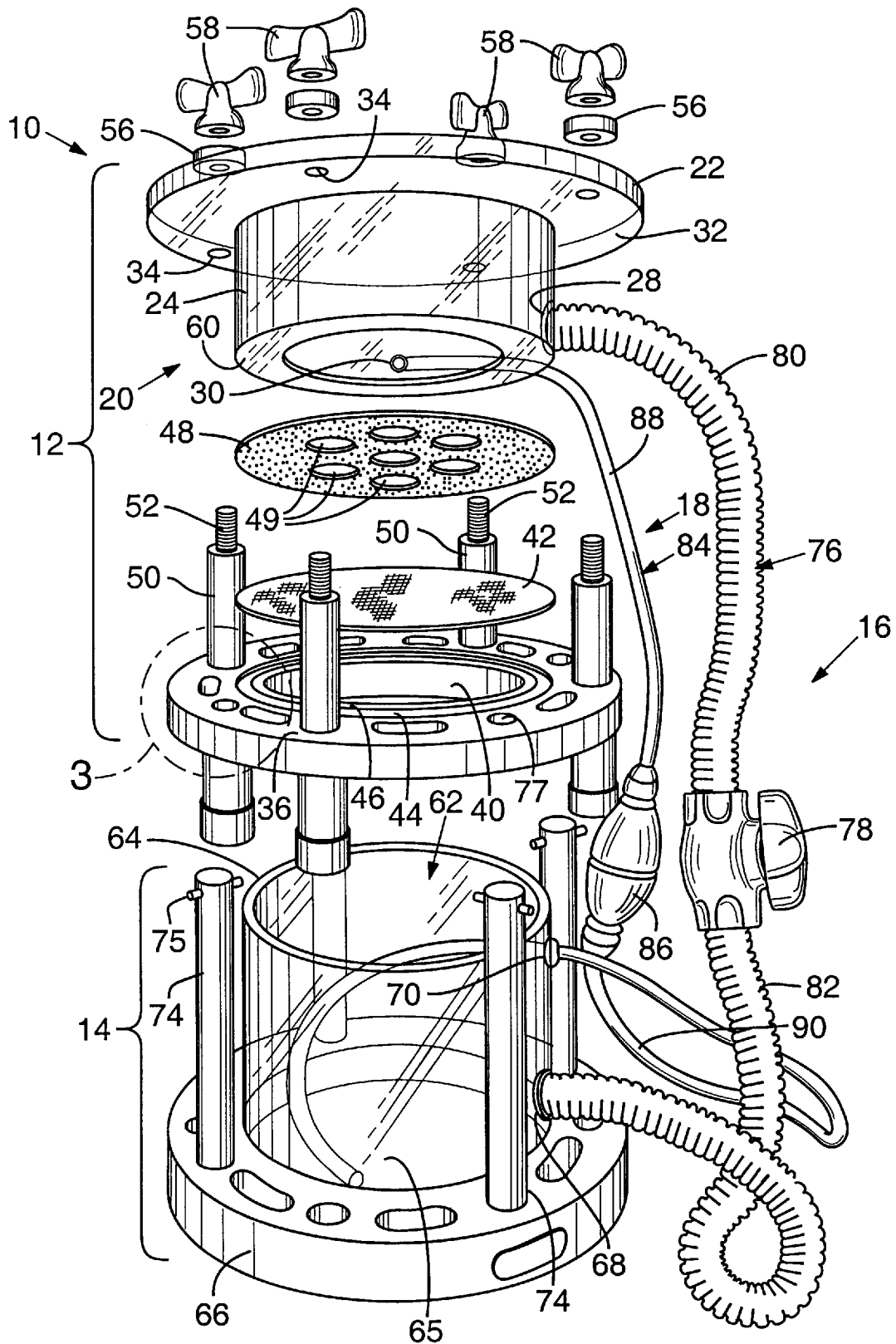
FIG. 1 is an exploded perspective view of the apparatus of the present invention in a preferred embodiment configuration.

A fabric testing apparatus 10 comprising a demonstration unit 12, a base unit 14, a first fluid transfer element 16 and a second fluid transfer element 18 is illustrated in the Figures. Demonstration unit 12 includes a demonstration reservoir 20 which is defined between a top plate 22, a wall 24 and a support plate 26. Wall 24 is preferably cylindrical in configuration and formed of a transparent plastic material such as an acrylic plastic. Wall 24 has a first hole 28 for fluid ingress and egress and a second hole 30 for fluid ingress and egress. Holes 28 and 30 are formed adjacent the lower edge of wall 24 and are spaced 90° apart around the perimeter of wall 24.

Top plate 22 also is preferably formed of a transparent acrylic plastic and is attached, for example by an adhesive, to one end of wall 24. Top plate 22 extends beyond the perimeter of the wall 24 to form a flange 32, which has through-holes 34 for use in assembling the demonstration unit. Support plate 26 likewise has a flange 36 extending beyond the perimeter of wall 24 and includes through holes 38 for use in assembling the demonstration unit. Support plate 26 is preferably formed from a conventional pipe flange, such as a four inch schedule 80 PVC pipe flange.

Figure 3:
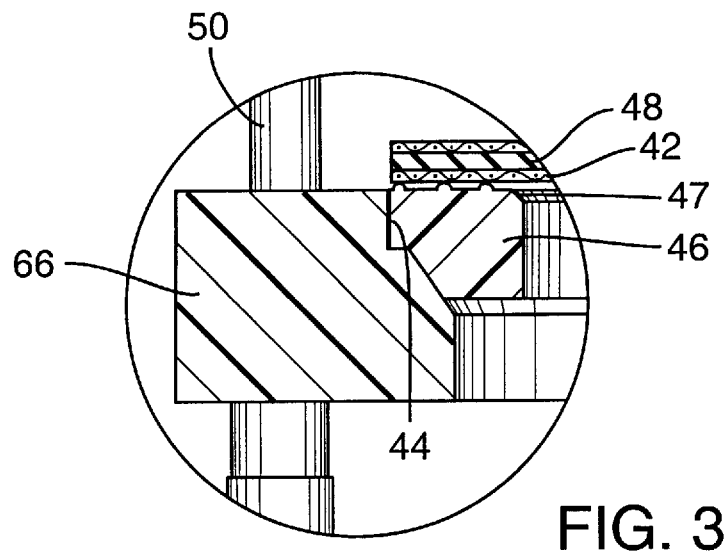
FIG. 3 is an enlarged cross-section through a compression ring retained in a groove in the support plate.
Figure 4:
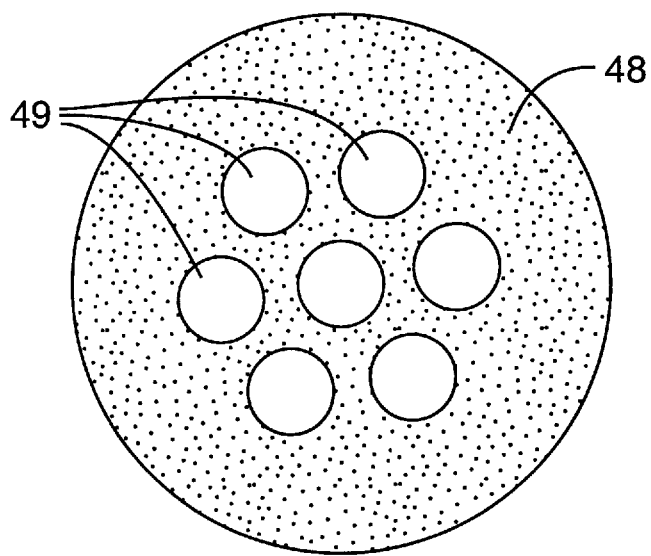
FIG. 4 is a plan view of a gasket placed over the test specimen.

Support plate 26 has a central opening 40, over which a fabric specimen 42 to be tested is placed. A compression ring 46 is placed in a groove 44 and has a cross-section with a depth greater than the depth of groove 44 so that the top of compression ring 46 extends out of groove 44, as seen in FIG. 3. A compression ring is typically provided with a PVC pipe flange and is typically made of the same material as the flange, for example schedule 80 PVC. The typically provided compression ring is shortened to an appropriate length extending slightly above groove 44, and the upper inside edge 47 is beveled to provide a contoured surface for protecting the fabric when the reservoir is filled with water, as seen in FIG. 3. This contouring prevents creation of stress points on the fabric which would compromise breathability tests by allowing air to pass through the stress points. A gasket 48 formed from a thin sheet of a flexible elastomer and having multiple holes 49 within the central region of the gasket is placed over test specimen. Gasket 48 is preferably formed of an eighth inch rubber with a cloth laminate sandwich construction to prevent the gasket from stretching out of shape. Holes 49 in gasket 48 are grouped around the center of the gasket in order to locate air flow paths through the fabric away from the inside edge of base 60 of demonstration reservoir 20.

Support pillars 50, which are preferably made of acrylic plastic rods, extend through holes 38 in flange 36 and through holes 34 in flange 32. Support pillars 50 are fixed within holes 38 in flange 36 by passing pillars 50 through the bottom of holes 38 until the larger diameter base 51 of pillars 50 contact the bottom of support plate 26. A clamping element secures top plate 22 with attached wall 24 to support plate 26. The clamping element is preferably formed of threaded rods 52 extending from the upper end of support pillars 50 and washers 56 and nuts 58.

Demonstration unit 12 is assembled by fitting compression ring 46 into groove 44, placing a swatch of test fabric specimen 42 over central opening 40 and compression ring 46. For example, if an apparel outerwear fabric is being tested, the outer surface of the fabric is placed to face upward into the interior of demonstration reservoir 20. Gasket 48 is placed on top of the outer surface of fabric specimen 42. Base 60 of wall 24 is placed on top of gasket 48. Support pillars 50 are inserted through holes 34 in top plate flange 32. The nuts 58 are thereafter tightened onto threaded rods 52 to form the assembled demonstration unit 12 and to form a water-tight seal around the perimeter of fabric specimen 42.

Figure 2:
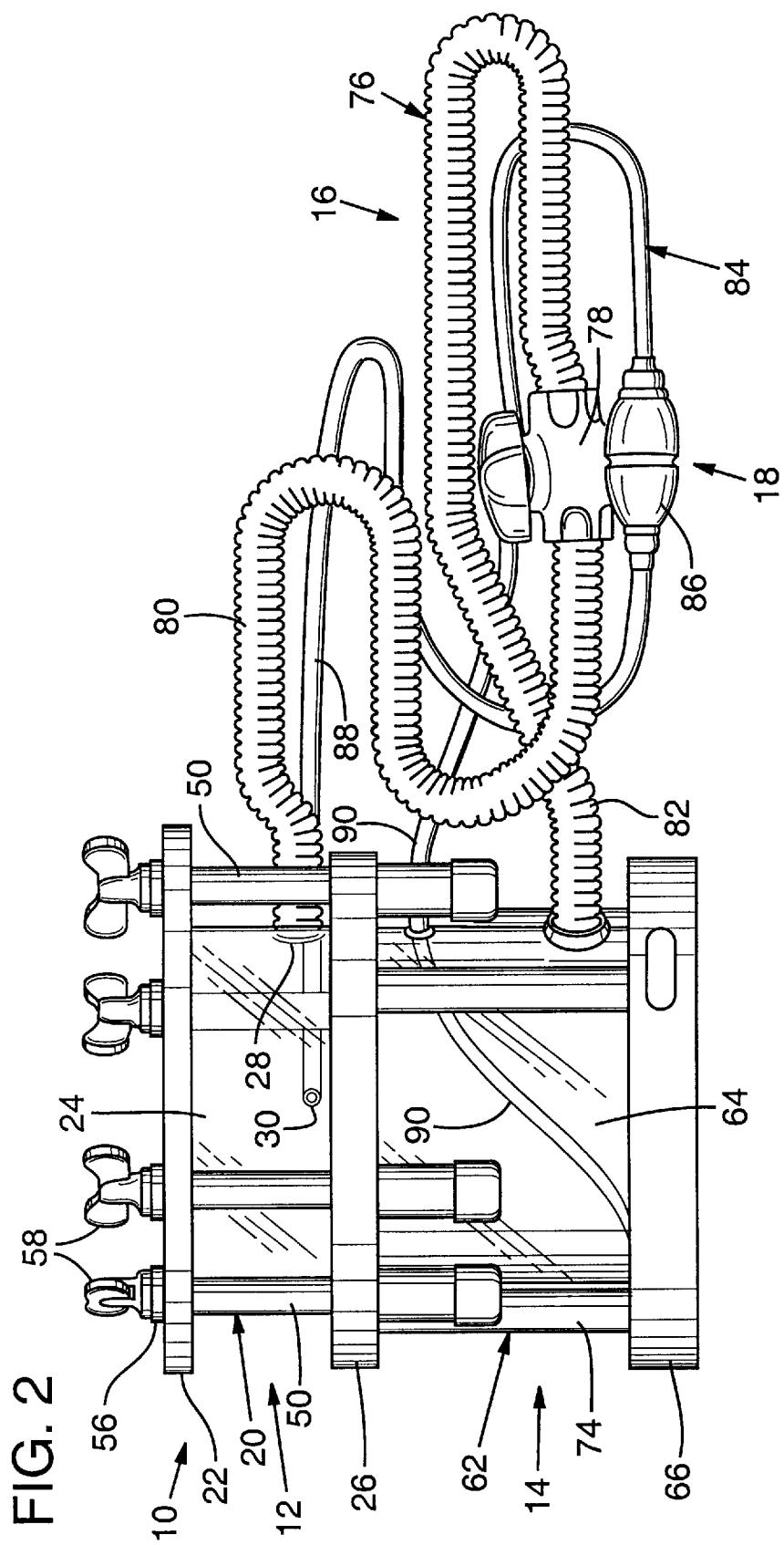
FIG. 2 is a side elevational view of the apparatus of FIG. 1, in an assembled condition.

Base unit 14 includes a base reservoir 62 defined between an encasing base cylindrical wall 64, a bottom wall 65 and a base plate 66. A first hole 68 for fluid ingress and egress, and a second hole 70 for fluid ingress and egress are formed through wall 64. Base wall 64 and bottom wall 65 are also preferably made of a transparent plastic acrylic material, with base wall 64 attached to bottom wall 65 by an adhesive to form a water reservoir. Base plate 66 is preferably made of a PVC plastic such as a schedule 80 PVC pipe flange. Base plate 66 is placed around the perimeter of base wall 64 and extends beyond the perimeter of base wall 64. Base pillars 74 are attached at one end to base plate 66 and extend perpendicular to the plane of the base plate. Base pillars 74 preferably extend above the upper end of base wall 64 and include support pins 75. FIG. 2 illustrates demonstration unit 12 supported on base unit 14. In this position, the upper ends of base pillars 74 pass through holes 77 in flange 36 of support plate 26 and the bottom of support plate 26 rests on pins 75.

The first fluid transfer element 16 is formed of a conduit 76 and a fluid valve 78 interposed in the fluid flow path of conduit 76. Conduit 76 preferably has a first flexible fluid conduit portion 80 extending from fluid ingress/egress hole 28 in wall 24 of demonstration reservoir 20 to fluid valve 78, and a second flexible fluid conduit portion 82 extending from fluid valve 78 to fluid ingress/egress hole 68 in wall 64 of base reservoir 62. The second fluid transfer element 18 is formed of second conduit 84 and a pump 86. Conduit 84 preferably includes a first flexible conduit portion 88 extending from fluid ingress/egress hole 30 in wall 24 of demonstration reservoir 20 to pump 86, and a second flexible conduit portion 90 extending from pump 86 to fluid ingress/egress hole 70 in wall 64 of base reservoir 62. Brass bulkhead fittings are fitted in ingress/egress holes 30 and 70. At fluid ingress/egress holes 28 and 68 a short length of plastic or acrylic tubing is glued and the ends of the fluid conduit portions 80 and 82 are placed over the tubing to form a water tight seal. Fluid conduit portions 80 and 82 are preferably at least three quarter inch I.D. to create adequate vacuum in the demonstration reservoir when water flows from demonstration reservoir 20 into base reservoir 62, with a total length of approximately four feet. Fluid conduit 76 is preferably made of a conventional three-quarter inch plastic vacuum hose. Fluid conduit 84 is preferably made of one quarter inch vinyl hose. Fluid valve 78 is preferably a conventional, manually operable on-off valve, such as a three-quarter inch valve made of schedule 80 PVC. Pump 86 is preferably a conventional, manually operable in-line fuel pump, such as used with outboard motors, with the flow direction being from base reservoir 62 to demonstration reservoir 20.

A method of demonstrating fabric characteristics is described below. First, fabric specimen 42 is placed on top of support plate 26 so that it extends over opening 40 and compression ring 46, gasket 48 is placed on top of fabric specimen 42 and demonstration reservoir 20 is lowered over fabric specimen 42. Thereafter, demonstration reservoir 20 is secured in position with nuts 58 being tightened on rods 52, in the manner described above. In this manner, the central region of fabric specimen 42 is exposed to the atmosphere and to view through opening 40. Base reservoir 62 is then filled with water. Fluid valve 78 is preferably closed, and then transparent demonstration unit 12 is placed physically lower than base unit 14, for example on the floor. Demonstration unit 12 is positioned on its side with fluid ingress/egress hole 28 at a twelve o'clock position; i.e. in an uppermost position. Fluid valve 78 is opened, and the water from the physically higher base reservoir 62 flows into the physically lower transparent demonstration reservoir 20 through both fluid conduits 76 and 84. Pump 86 is used to pump water from base reservoir 62 into transparent demonstration reservoir 20 to assure that it is completely filled with water and all air is purged from demonstration reservoir 20. Fluid valve 78 is preferably closed and then the transparent demonstration unit 12 is elevated and turned over so that the inner surface of fabric specimen 42, and support plate 26, both are now facing up, to visually inspect the exposed portion of the fabric and demonstrate whether the fabric specimen has not let water through, i.e. is waterproof.

To test and demonstrate the breathability of fabric specimen 42, the waterfilled demonstration unit 12 is positioned with the inner surface fabric specimen 42, and support plate 26, both facing down, and base unit 14 is placed physically lower than demonstration unit 12. The action of pump 86, causes the water in demonstration reservoir 20 to be slightly pressurized. Sufficient water is initially placed in base reservoir 62 so that after water has filled demonstration reservoir 20, water also fills both conduits 76 and 84, and water also remains in the lower portion of base reservoir 62. Fluid valve 78 is opened, and the water from the physically higher transparent demonstration reservoir 20 is allowed to flow into the physically lower base reservoir 62 with the action of the water flowing from the higher to the lower reservoir creating a vacuum inside the physically higher transparent demonstration reservoir 20. If the fabric specimen is breathable, air is drawn into transparent demonstration reservoir 20 through the fabric and is visible as rising bubbles which visually demonstrates the fabric's breathability.

Numerous characteristics and advantages of the invention have been set forth in the foregoing description, together with details of the structure and function of the invention, and the novel features thereof are pointed out in the appended claims. The disclosure, however is illustrative only, and changes may be made in detail, especially in matters of shape, size and arrangement of parts, within the principle of the invention, to the full extent indicated by the broad general meaning of the terms in which the appended claims are expressed. For example, the apparatus can function solely by gravity by eliminating the second fluid conduit and pump.

What is claimed:

1. A fabric testing apparatus comprising, a demonstration unit, a base unit separate from and moveable with respect to said demonstration unit, and a fluid transfer element in fluid communication between said demonstration unit and said base unit, at least a portion of said fluid transfer element being flexible and having a length sufficient to allow said demonstration unit to be positioned both above and below said base unit;

said demonstration unit having a demonstration reservoir and a test fabric specimen mounting element, said demonstration reservoir having an encasing demonstration reservoir wall and a top plate connected to the wall for containing a liquid, said wall being transparent, and having a first hole for fluid ingress and egress, said test fabric specimen mounting element having a support plate to support a test fabric specimen wherein the test fabric specimen is partially exposed to atmosphere and visible;

said base unit having a base reservoir with an encasing base reservoir wall and a bottom wall for containing a liquid, said base reservoir wall having a hole for fluid ingress and egress; and said fluid transfer element including at least one fluid conduit extending from the fluid ingress/egress hole in said demonstration reservoir wall to the fluid ingress/egress hole in said base reservoir wall and a valve in the flow path of said fluid conduit to control the flow of fluid through said fluid conduit, said valve having an open position for directing the flow of liquid from said base reservoir to said demonstration reservoir to fill said demonstration reservoir with the liquid with said demonstration reservoir positioned below said base reservoir to thereby demonstrate the waterproofness of the test fabric specimen and said open position of said valve directing the flow of liquid from the demonstration reservoir to said base reservoir, drawing air through the test fabric specimen and into said demonstration reservoir to demonstrate the breathability of the test fabric specimen with the demonstration reservoir positioned above said base reservoir.

2. The fabric testing apparatus of claim 1 including a second fluid transfer element in fluid communication between said demonstration unit and said base unit, said second fluid transfer element including a second fluid conduit extending from a second fluid ingress/egress hole in said demonstration reservoir wall to a second fluid ingress/egress hole in said base reservoir wall and a pump in the flow path of said second fluid conduit for pumping water from said base reservoir to said demonstration reservoir to fill said demonstration reservoir with liquid and purge air therefrom.

3. The fabric testing apparatus of claim 1 or 2 wherein said support plate has an opening over which a test specimen is to be placed, and a compression ring is supported adjacent said opening, said demonstration reservoir wall having a base for placement over the test specimen and said compression ring, and a clamping mechanism for securing said demonstration reservoir wall in a fluid tight manner over the test specimen and said compression ring.

4. The fabric testing apparatus of claim 3 wherein said support plate includes a support plate flange portion extending outward of said opening and said top plate includes a demonstration reservoir flange portion extending outward of said demonstration wall, and said clamping mechanism includes pillars extending between said support plate flange portion and said demonstration reservoir flange portion, and clamps for removably connecting said support plate to said demonstration reservoir through said pillars.

5. The fabric testing apparatus of claim 4 wherein said support plate flange and said demonstration reservoir flange each have aligned holes through which said pillars extend and said clamps are formed by threaded rods extending from at least one end of said pillars and nuts for tightening on to said threaded rods.

6. The fabric testing apparatus of claim 3 including a gasket supported between the test specimen and said base of demonstration reservoir wall to form a fluid-tight and air-tight seal therebetween, said gasket having at least one hole located over the test fabric specimen.

7. The fabric testing apparatus of claim 4 wherein said support plate and said top plate of said demonstration reservoir are both circular, and said demonstration reservoir wall is cylindrical.

8. The fabric testing apparatus of claim 1 wherein said fluid conduit includes a first fluid conduit portion extending from the fluid ingress/egress hole in said demonstration reservoir wall to a first end of said valve and a second fluid conduit portion extending from the other end of said valve to the ingress/egress hole in said base reservoir wall, and at least one of said first and second fluid conduit portions being formed of a flexible material.

9. The fabric testing appartus of claim 1 wherein said base reservoir includes a base reservoir flange extending outward of said base reservoir wall, and a plurality of base support pillars extend upward from said base reservoir flange for alignment with holes in said support plate, and support pins being attached adjacent the top of said base support pillars, whereby said demonstration reservoir can be moveably supported above said base reservoir by inserting the top ends of said base support pillars into said aligned holes in said support plate and supporting the bottom of said support plate on said pins.

10. A method of demonstrating fabric characteristics comprising the steps of:

securing a fabric specimen to a support of a demonstration unit, wherein a portion of the fabric specimen is exposed to the atmosphere and to view;

filling a base reservoir of a base unit with water, said base reservoir being coupled to a demonstration reservoir of the demonstration unit by a flexible fluid conduit;

placing said demonstration unit physically lower than said base unit;

flowing the water from the physically higher base reservoir into the physically lower demonstration reservoir and into contact with the fabric specimen and filling the demonstration reservoir with water;

positioning the demonstration unit so that the deposed portion of the fabric specimen is visible, to demonstrate whether the fabric specimen is waterproof;

placing the water-filled demonstration unit, with the fabric specimen at the bottom of the demonstration unit, physically higher than the base unit; and letting the water from the physically higher demonstration reservoir flow into the physically lower base reservoir, the action of the water flowing from the higher to the lower reservoir creating a vacuum inside the physically higher demonstration reservoir, wherein air is drawn into the demonstration reservoir through a breathable fabric and is visible as rising bubbles in the water through a transparent wall of the demonstration reservoir which visually demonstrates the fabric's breathability.

11. The method of demonstrating fabric characteristics of claim 10 including the steps of:

closing a fluid valve in said fluid conduit, prior to placing said demonstration unit lower than said base unit; and, thereafter opening said fluid valve to allow the water from the physically higher base reservoir to flow into the physically lower demonstration reservoir.

12. The method of demonstrating fabric characteristics of claim 11 including the steps of:

forcing air out of the demonstration reservoir as the reservoir fills with water by pumping water into the demonstration reservoir until the demonstration reservoir is filled with water; and, thereafter closing the fluid valve.

* * * * *